United States Patent
Schuster et al.

(10) Patent No.: US 6,226,349 B1
(45) Date of Patent: May 1, 2001

(54) X-RAY ANALYSIS APPARATUS WITH A GRADED MULTILAYER MIRROR

(75) Inventors: Manfred Schuster; Herbert Goebel, both of Munich; Carsten Michaelsen, Geesthacht; Ruediger Bormann, Rosengarten, all of (DE)

(73) Assignee: Bruker AXS Analytical X-Ray Systems GmbH, Karlsruhe (DE)

( * ) Notice: Subject to any disclaimer, the term of this patent is extended or adjusted under 35 U.S.C. 154(b) by 0 days.

(21) Appl. No.: 09/356,346

(22) Filed: Jul. 19, 1999

(30) Foreign Application Priority Data

Jul. 25, 1998 (DE) .............................. 198 33 524

(51) Int. Cl.[7] ...................... G01N 23/207; G01N 23/223
(52) U.S. Cl. ................................. 378/84; 378/81
(58) Field of Search .................. 378/84, 81, 82

(56) References Cited

U.S. PATENT DOCUMENTS

| | | |
|---|---|---|
| 4,525,853 | 7/1985 | Keem et al. . |
| 4,567,605 | 1/1986 | Bartels . |
| 4,684,565 | 8/1987 | Abeles et al. . |
| 4,924,490 | 5/1990 | Hashimoto et al. . |
| 5,646,976 | 7/1997 | Gutman . |
| 6,069,934 | * 5/2000 | Verman et al. ............... 378/73 |

FOREIGN PATENT DOCUMENTS

| | | |
|---|---|---|
| 4407278A1 | 9/1995 | (DE) . |
| WO95/22758 | 8/1995 | (WO) . |

OTHER PUBLICATIONS

Hogrefe, H. et al.: "Soft x–ray scattering from rough surfaces: experimental and theoretical analysis" in Applied Optics, vol. 26, No. 14, Jul. 1987, pp. 2851–2858.

Bruson, A. et al.: X–ray scattering from nonideal multilayer structures: Calculations in the kinematical approx. in: J. Applied Physics 77 (3), Feb. 15 1995, p. 1001–1009.

(List continued on next page.)

Primary Examiner—Robert H. Kim
Assistant Examiner—Drew A. Dunn
(74) Attorney, Agent, or Firm—Paul Vincent

(57) ABSTRACT

An X-ray analysis apparatus having a curved paraboloid-shaped curved graded multilayer Bragg reflector (5) is characterized in that the layers of the reflector (5) are directly introduced onto a concave curved surface of a paraboloid-shaped hollow substrate and a maximum allowable shape deviation for the concave substrate surface facing the reflector is $\Delta p = \sqrt{2px}\, \Delta\theta_R$, and having a maximum allowable waviness $$\frac{\Delta y}{\Delta x} = \frac{1}{2}\Delta\theta_R$$

and a maximum allowable roughness $\Delta y = d/2\pi$, preferentially $\Delta y \leq 0.3$ nm, wherein the X radiation (7) impinges on the curved surface of the reflector (5) at an angle of incidence $0° < \theta \leq 5°$ with the period thickness d of the reflector layer towards the paraboloid opening increasing in the x direction in accordance with $$d = \frac{\lambda}{2} \frac{1}{(1 - \delta/\sin^2\theta)\sin\theta} \text{ and } \theta = \text{arccot}\sqrt{\frac{2x}{P}},$$

wherein the deviation $\Delta d/\Delta x$ is less than $d/(2x)$. In this fashion, the transmission of the analysis apparatus is substantially improved as is the reliability and the lifetime, with reduced manufacturing difficulty and expense.

24 Claims, 10 Drawing Sheets

OTHER PUBLICATIONS

Schuster, M.eta al.:"Parallel–beam coupling into channel–cut monochromators using curved graded multilayers" in J. Phys. D: Appl.Phys. 28 (1995) A270–275.

Schuster, M. et al.: "Application of Graded Multilayer . . . " in: Advances in X–Ray Analysis,vol. 39,Plenum Press,1997.

Company brochure "Mirrors for Synchrotron Radiation" by ZEISS–Germany, APS–Division, Oberkochen, 1992.

Schuster, M. et al.: Göbel Mirrors–a Breakthrough for Applications of X–ray Diffraction in: Bruker Report No. 145/98 p. 9–13.

Proceedings of SPIE–The International Society for Optical Eng. vol. 563 "Application of Thin–Film Multilayered Structure to Figured X–Ray Optics" (1985), pp. 114–134.

J. Phys. D: Applied Physics 30 (1997) 3167–3186: C.Michaelsen et al.: "Investigating the thermodynamics and kinetics of thin–film reactions by differential scanning calorimetry".

* cited by examiner

X-RAY ANALYSIS APPARATUS WITH A GRADED MULTILAYER MIRROR

This application claims Paris Convention Priority of German Patent Application No. 198 33 524.5 filed Jul. 25, 1998, the complete disclosure of which is hereby incorporated by reference.

BACKGROUND OF THE INVENTION

The invention concerns an X-ray analysis apparatus, a curved Bragg reflector for use in the apparatus, a method for manufacturing the curved Bragg reflector and an apparatus for carrying out the method, the apparatus having a source emitting X-rays a sample to be analyzed a detector sensitive to X-ray radiation beam-shaping and/or beam-limiting means a curved multilayer Bragg reflector disposed in the optical path between the source and the sample including a periodically repeated sequence of layers, wherein a period comprises at least two individual layers A, B having differing index of refraction decrements $\delta_A \neq \delta_B$ and with thicknesses $d_A$ and $d_B$, wherein the period thickness, e.g. the sum $d=d_A+d_B+d_C+ \ldots$ of the individual layers A, B, C, $\ldots$ of one period, changes constantly along an x direction and wherein the reflector is curved in such a fashion that it forms a partial surface of a paraboloid at the focal line or focal point of which the source or an image of the source is disposed so that a parallel beam is produced subsequent to reflection.

An X-ray analysis apparatus of this kind is known in the art from WO 95/22758.

X-ray analysis apparatus include, e.g. X-ray spectrometers and X-ray-diffractometers and serve for the non-distructive analysis of solid, powder and liquid samples. Diffractometers, in particular powder diffractometers, normally utilize focussing beam configurations to guarantee efficient use of the X-ray beam illuminating the sample. These kinds of apparatus use, among other things, multilayer reflectors at which Bragg reflexion of the incident light occurs in order to monochromatize the X-ray radiation from the source. However, if reflectors consisting of planar homogeneous multilayers are used, the Bragg condition only holds for one single incident angle per irradiated wavelength so that the incident beam must be highly parallel.

In contrast thereto, the so-called graded multilayer mirror provides an improvement thereto with which the layers utilized exhibit a monotonically increasing period thickness on a flat substrate to make a divergent beam of incident radiation monochromatic.

An additional substantial improvement is achieved through use of a curved multilayer mirror as described in the above quoted WO 95/22758.

The curvature of this parabolic mirror is thereby tuned to a particular wavelength so that, in addition to a monochromatization, the incident radiation is focussed and a larger solid angle can be accepted from the source with the exiting beam made parallel.

This type of curved graded multilayer mirror is made by successive deposition of layers of laterally varying thicknesses on a flat substrate, generally a silicon wafer, with subsequent bending of the substrate having the multilayer reflector introduced thereon and glueing of this configuration onto a usually curved substrate holder, usually comprising aluminium or made from invar.

A curved reflector of this kind has, however, the disadvantage of being highly sensitive to, among other things, extremely slight geometric errors, since the radiation from the source impinges on the surface of the mirror at grazing incidence angles in the order of 1°. For this reason, even extremely small dust particles or irregularities on the surface of the substrate have devastating effects on the required shape of the mirror. These effects are discussed e.g. in J. Phys. D. Appl. Phys. 28 (1995) A 270 through A 275.

Additional substantial errors due to stresses or relaxation effects in the substrate are present in the edge regions. Even a deviation in the order of 30" from the intended parabolic curve which would be caused by a shape deviation of 10 $\mu$m over a length of approximately 60 mm, leads to substantial angular errors which affect the divergence and homogeneity of the reflected beam and its photon flux density.

Accordingly, even a particle having a size of a grain of dust disposed on the surface of the substrate holder is sufficient to significantly distort the multilayer mirror introduced thereon and thereby the overall optics. Stresses and strains present on the ends of the wafer associated with an inhomogeneous force distribution between the edge regions and the center, cause the edges to extend to a greater or lesser degree substantially in a straight fashion away from the center or even curve in the wrong direction so that, in these regions, incident light is reflected in a wrong direction.

An additional, non-negligible source of error is caused by the use of glue for attaching the substrate with the associated multilayer onto a mechanical holder. The loading with X-ray radiation during operation often leads to a foaming of the glue and thereby to a deformation of the entire mirror surface so that the associated reflector can no longer be used.

A high degree of manufacturing effort and skill is required in order to produce a curved multilayer Bragg reflector of the conventional kind according to WO 95/22758. The initially flat "mirror face surface" is introduced onto a curved reference surface made from mirror glass, using an optical attachment procedure, and remains fixed in this location with the correct curvature by means of adhesion. Glueing onto a suitable substrate holder is then carried out.

Finally, the conventional curved multilayer Bragg reflector only brings an increase in reflected photon flux density of a factor of 6 by rendering the incident diverging beam parallel using the same arrangement as described in M. Schuster and H. Göbel, J. Phys. D: Applied Physics 28 (1995) A270–A275. This is disadvantageous, since the theoretically achievable value is an improvement of a factor of 30. The difference between the actual and the theoretical effect can be explained by the above mentioned geometric errors due to the manufacturing and construction of the X-ray mirror.

In contrast thereto, it is a purpose of the present invention to create an X-ray analysis apparatus of the above mentioned kind with as little technical effort and expense as possible with which the transmission is substantially improved and the reliability and lifetime of the components is substantially increased.

SUMMARY OF THE INVENTION

This purpose is achieved in accordance with the invention in that layers of the reflector are directly evaporated, sputtered or grown on a concave curved surface of a paraboloid-shaped hollow substrate, wherein the curvature of the concave substrate surface in an xy cross section is given by $$y^2 = 2px \tag{1}$$

with $$0.02 \text{ mm} < p < 0.5 \text{ mm},$$

preferentially $$p \approx 0.1 \text{ mm},$$

and the concave substrate surface facing the reflector has a maximum permissible shape deviation of $$\Delta p = \sqrt{2px} \cdot \Delta \theta_R \quad (2)$$

wherein $\Delta\theta_R$ is the full width half maximum of the Bragg reflexion of the reflector and lies in the region $$0.01° < \Delta\theta_R < 0.5°,$$

preferentially $$0.02° < \Delta\theta_R < 0.20°,$$

and the concave surface of the substrate facing the reflector has a maximum allowable waviness (angle error) of $$\frac{\Delta y}{\Delta x} = \frac{1}{2} \Delta \theta_R \quad (3)$$

and the concave substrate surface facing the reflector has a maximum allowable RMS roughness of $$\Delta y = d/2\pi,$$

preferentially $$\Delta y \leq 0.3 \text{ nm} \quad (4).$$

and the X-ray radiation is incident on the curved surface of the reflector at an incident angle $0° < \theta \leq 5°$,
and the period thickness d changes along the x direction in such a fashion that the X-ray radiation of a particular wavelength λ from a point or line X-ray source is subject to Bragg reflection independent of the point of incidence (x, y) on the reflector, wherein the period thickness d in the x direction increases towards the paraboloid opening in accordance with $$d = \frac{\lambda}{2} \frac{1}{(1 - \delta/\sin^2\theta)\sin\theta} \quad \text{with} \quad (5)$$

$$\theta = \text{arccot}\sqrt{\frac{2x}{p}} \quad (6)$$

wherein δ is the decrement in the average index of refraction of the multilayer Bragg reflector
and the deviation per length $\Delta d/\Delta x$ of the period thickness d defined in equations (5) and (6) is smaller, at all points of the multilayer Bragg reflector along the x direction, than $$\frac{\Delta d}{\Delta x} = \frac{1}{2} \frac{d}{x} \quad (7)$$

and wherein the period thickness d is given by $$1 \text{ nm} \leq d \leq 20 \text{ nm},$$

wherein the number, N, of periods is $$10 < N < 500,$$

preferentially $$50 \leq N \leq 100,$$

and the following relationship holds for the energy E of the photons of the X-ray radiation $$0.1 \text{ keV} < E < 0.1 \text{ MeV}.$$

The direct deposition of reflector layers on a concave curved surface facilitates substantially reduced manufacturing tolerances with respect to the curvature of the mirror and the avoidance of errors in the layers, wherein the manufacturing effort and expense during assembly is substantially reduced, since the substrate already has a curved surface and must not be first curved after placement on the substrate holder. In principle, the substrate holder can be entirely eliminated to effect an overall reduction in the number of components required. The use of an additional holder body and attachment of the substrate thereto using glue is also less critical, since the unavoidable aging effects and degeneration effects associated with exposure of the glue to radiation are substantially less critical: the side of the substrate facing away from the layer can be flat and the connection to a substrate holder must not be effected under force so that no substantial encroachment on the mirror is caused by slight changes in the glue layer throughout the course of time.

For reasons of completeness, it is mentioned here that a "paraboloid shape" includes both extreme cases of the rotational paraboloid and the parabolic cylinder. The expression also includes ellipsoidal, spherical, hyperboloid, logarithmic spiral and even planar mirrors satisfying the above cited conditions.

The precise variation of the period thickness d in the x direction is described in equations (5) and (6). Manufacturing simplifications, such as a linear approximation to the relationship between d and x, can be effected as a variation of the invention described herein.

In an advantageous embodiment of the invention, the substrate is made from amorphous or polycrystalline material. Curved surfaces of these materials are simpler to machine than those of crystalline material and are substantially less expensive since they have been widely used in optical applications for many decades.

In an advantageous improvement of this embodiment, the substrate is made from glass, amorphous silicon, ceramic material, quartz glass or plastic so that the concave paraboloid surface of the substrate can be ground or polished therein with extremely high precision using an acceptable degree of manufacturing effort and expense. The layered structure of the curved reflector is then deposited onto the concave substrate surface by evaporation, sputtering or growth.

An embodiment of the X-ray analysis apparatus in accordance with the invention is particularly preferred in which the substrate has a thickness D to act as a mechanical support body of stable shape for the curved reflector, wherein D is preferentially 0.05 L<D<0.5 L with L=the length of the substrate in the x direction.

In this fashion, the mechanical substrate holder component which had been necessary up to now becomes superfluous. This avoids an additional source of error as well as increased manufacturing difficulty and expense. In addition, there is no need to glue the substrate and the substrate holder so that the above mentioned problems concerning aging of this glue layer can no longer occur.

A number n of individual layers A, B, C, . . . per period is preferentially: $2 \leq n \leq 4$.

The X-ray analysis apparatus in accordance with the invention is preferentially part of a high-resolution spectrometer or diffractometer.

In an additional preferred configuration, the individual layer thicknesses of a period are chosen in such a fashion that second order diffraction vanishes. With monochromators, in addition to first order diffraction, higher order diffractions (the second or the third order . . . photon energies) are transmitted. In many applications, higher diffraction orders are undesirable, in particular second order diffraction. If the period comprises two individual layers A and B, a structural extinction of the second diffraction order can be approximately achieved by choosing $d_A=d_B$. A more detailed approach, taking into consideration refraction and absorption effects, requires an additional condition for extinguishing second order diffraction:

$$d_A = d_B \cdot k \text{ with } 1 \leq k \leq 1.05,$$

wherein

A is the individual layer having the higher density and

B the individual layer having the lower density.

An additional preferred embodiment is distinguished in that a collimator is disposed in the optical path between the source and the sample and the detector, the collimator having fins disposed parallel with respect to each other and directed towards the beam of X-ray radiation.

In an additional advantageous embodiment of the X-ray analysis apparatus in accordance with the invention, a first monochromator is disposed in the optical path between the curved reflector and the sample which can preferentially be configured as a multiple monochromator, in particular as a multiple "channel-cut" monochromator of type (+−−+).

An additional advantageous embodiment is distinguished by a second planar or curved multilayer Bragg reflector disposed in the optical path between the curved reflector and the sample.

An embodiment is also advantageous with which a second monochromator is disposed in the optical path between the sample and the detector which can, in particular, be configured as a planar crystal monochromator.

An improvement is particularly advantageous which has a second curved multilayer Bragg reflector having the same construction as the first reflector with its paraboloid opening being directed towards the sample, wherein a slit is positioned at the focal point of the second reflector between the second reflector and the detector.

The combination of the second multilayer Bragg reflector with the slit at the focal point effects an analyzer configuration which facilitates the selection of X-ray radiation of a particular wavelength and angle, in accordance with its exiting direction. This, in particular, allows radiation diffusely deflected from the sample to be selectively detected in dependence on its wavelength and scattering direction.

A curved multilayer Bragg reflector having the above described features for installation into an X-ray analysis apparatus in accordance with the invention is also within the framework of the invention.

The Bragg reflector in accordance with the invention preferentially comprises a first layer having a heavy element and a second layer having a light element, wherein said heavy element is selected from a group consisting of V, Cr, Mn, Fe, Co, Ni, Cu, Nb, Mo, Pd, W, Pt, Ir, and Au and the light element being selected from the group consisting of Be, B, C, N, O, Mg, Al and Si. In an advantageous embodiment of the invention, the first layer comprises a heavy material and the second layer comprises a light material with the light material being selected from the group consisting of $B_4C$, BN, $Al_2O_3$, $Si_3N_4$, and $SiO_2$.

Although, in accordance with the invention, the mirror Bragg reflectors can be produced using W-based multilayers such as W/C, W/$B_4$C, or W/Si, improved spectral resolution (in particular improved suppression of unwanted wavelengths such as the Kβ) can be obtained by using reflector materials having low absorption for Kα radiation and high absorption for Kβ radiation. Such materials include $WSi_2$ or other mixtures of W and Si, preferentially combined with Si as the spacer. Such material combinations lead to reduced absorption and higher resolution. In particular, Ni and Cu can be used for Cu Kα radiation, Fe, Cu, Ni, and Co for CoKα radiation, Mn, Cu, Ni, Co, Fe for FeKα radiation, V, Cu, Ni Co, Fe, Mn, Cr for CrKα-radiation and/or Mo, Zr, Nb, and Rh for MoKα radiation. These materials have absorption edges above the desired X-ray energies and therefore effect improved spectral resolution as well as improved intensity.

As summarized in the subsequent table, Ni can be used for Cu-Kα radiation, Fe for CoKα radiation, Mn for FeKα radiation, V for CrKα radiation, Zr and Nb for MbKα radiation, and Rh and Pd for AgKα radiation. These latter materials have absorption edges between the desired Kα and the undesired Kβ emission lines to therefore lead to high intensity and to a further improvement in spectral purity due to the additional edge filtering effect. The heavy materials mentioned above are favorably combined with lighter space materials such as C, $B_4$C, BN, Mg, Al and Si or alloys containing these materials such as $Al_2O_3$ or $Si_3N_4$.

The following table shows selection of elements suited for the heavy element layer of multilayers in dependence on the X-radiation to be used. In the column of the heavy elements, the mass absorption coefficient increases with the atomic number, i.e. the element with the lowest atomic number in each line is the best suited from the point of view of absorption.

| Radiation/Target | Heavy elemements with low absorption (atomic number Z) | Element suited as Kβ filter (atomic number Z) |
| --- | --- | --- |
| Ti radiation | Ti (22), V (23), Cr (24), . . . | none |
| Cr radiation | V (23), Cr (24), Ni (28), Cu (29) . . . | V (23) |
| Fe radiation | Mn (25), Fe (26), Co (27), Ni (28), Cu (29), . . . | Mn (25) |
| Co radiation | Fe (26), Co (27), Ni (28), Cu (29), . . . | Fe (26) |
| Cu radiation | Ni (48), Cu (29), . . . | Ni (28) |
| Mo radiation | Zr (40), Nb (41), Mo (42), Rh (45), Pd (46), Ag (47) . . . | Zr (40), Nb (41) |
| Ag radiation | Rh (45), Pd (46), Ag (47), Sn (50), . . . | Rh (45), Pd (46) |

The invention also concerns a method for producing a Bragg reflector and apparatus thereby, the reflector having a curve multilayer structure comprising at least two individual layers A, B, having differing index of refraction decrements, with thicknesses $d_A$ and $d_B$, wherein a period thickness $d=d_A+d_B+d_C+$ . . . of individual layers A, B, C, . . . changes monotonically in an x direction. The method comprises the steps of mounting a substrate, having a parabolic substrate surface, for rotation about an axis extending substantially normal to a region of said substrate surface, irradiating said substrate surface with a particle beam of heavy compound sputtered material emanating from a first sputter source, said first sputter source disposed at a first side of the axis, wherein the particle beam of heavy compound has a direction forming a first acute angle with respect to the axis, rotating said substrate about said axis through substantially 180°, and then irradiating said substrate with a particle beam of light compound sputtered material emanating from a second sputter source, the second sputter source disposed at a second side of said axis opposite the first side, with the particle beam of light compound having a direction forming a second acute angle relative to the axis.

The asymmetric geometry of the two sputter sources permits a changing thickness of the layers in the x direction which can be varied by adjusting the solid angles relative to the source at various positions along the substrate.

In an improved embodiment of this method and the apparatus, means are provided for focussing, collimating, and blocking the particle beam of heavy compound and the particle beam of light compound. This improvement allows for better control of the geometry relative to the respective source to thereby control the deposition of the material.

By repetition of the procedure outlined above, a plurality of layers can be formed.

In a preferred embodiment of the method and the apparatus producing the reflector, the angles of the two sputter sources are substantially equal to each other.

Further advantages of the invention can be derived from the description and the drawing. The above mentioned features and those to be described further below can be utilized in accordance with the invention individually or collectively in arbitrary combination. The embodiments shown and described are not to be considered exhaustive enumerations, rather have exemplary character only for illustration of the invention.

The invention is shown in the drawing and will be described more closely with reference to embodiments.

DESCRIPTION OF THE PREFERRED EMBODIMENT

Figure 1:
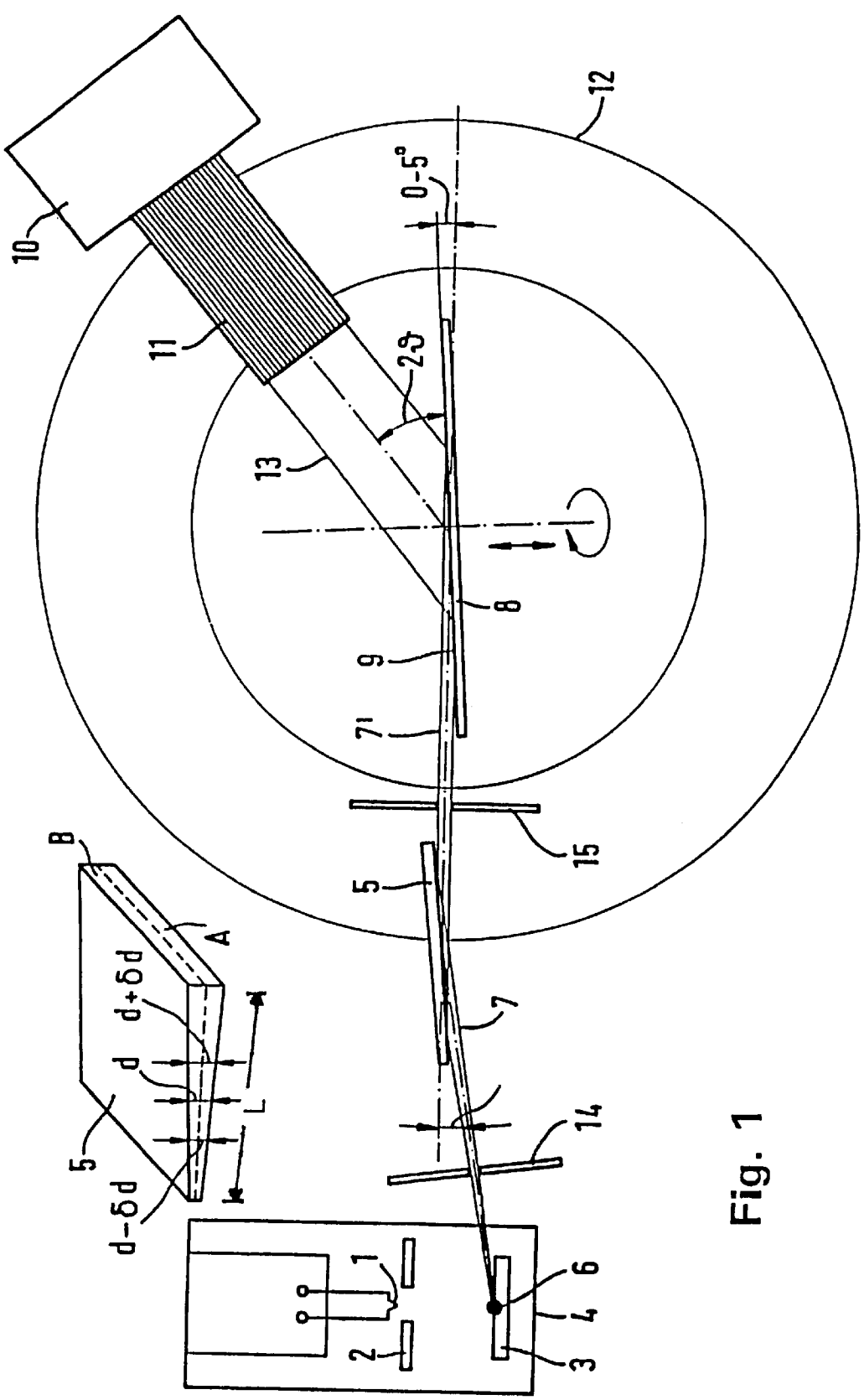
FIG. 1 shows a first embodiment of the X-ray analysis apparatus in accordance with the invention.

The thin film diffractometer schematically shown in FIG. 1 includes an X-ray tube 4 comprising a filament 1, a focussing electrode 2, and an anode 3, a parabolically curved multilayer Bragg reflector 5 for parallelization and deflection of the X-ray radiation 7 diverging from the line-shaped electron focus 6 on the anode 3 in the direction towards the thin film sample 9 disposed a glass substrate 8, a detector 10 (e.g. a proportional counter, a scintillation counter etc.) as well as a collimator upstream of the detector 10. The fins of the collimator 11 are oriented parallel to each other and are directed towards the sample 9 borne in the center of the measurement circle 12 in a rotatable and height-adjustable fashion. Therefore, only the X-ray radiation 13 scattered from the sample at a certain defined angle $2\theta$ is incident on the detector 10 as a nearly parallel beam. The divergence of the radiation 13 detected by the detector 10 thereby depends on the collimator used and assumes typical values of 0.1 to 0.4°. In addition, the diffractometer has adjustable collimators 14, 15 which limit the cross-section of the primary X-ray beam 7 and that of the parallel beam 7' illuminating the sample 9, in the horizontal direction.

The diffractometer in accordance with the invention has a curved multilayer Bragg reflector 5 X-ray mirror for production of the parallel monochromatic beam 7'. This paraboloid X-ray mirror, schematically represented in section in the upper portion of FIG. 2, contains a periodically repeating sequence of layers of materials A and B having index of refraction decrements $\delta_A \neq \delta_B$, wherein the number of individual layers within a period is at least two. The individual layers are preferentially produced by sputtering, evaporation or growth of the corresponding materials A and B, e.g. on a very smooth, preferentially ground and polished concave curved surface of a paraboloid-shaped hollowed substrate S, wherein the layers can be amorphous or crystalline. By way of example, the material combinations A/B:Mo/$B_4$C, Re/Si, Re/C, W/Si, W/C, Ta/Si, W/Be, Mo/Be, Mo/Si, Mo/C, Ni/C, Au/C, AuPd/C, ReW/B, ReW/C, Al/Be or V/C can be used for creating a multilayer Bragg reflector 5 having a periodic sequence of two individual layers.

Figure 2:
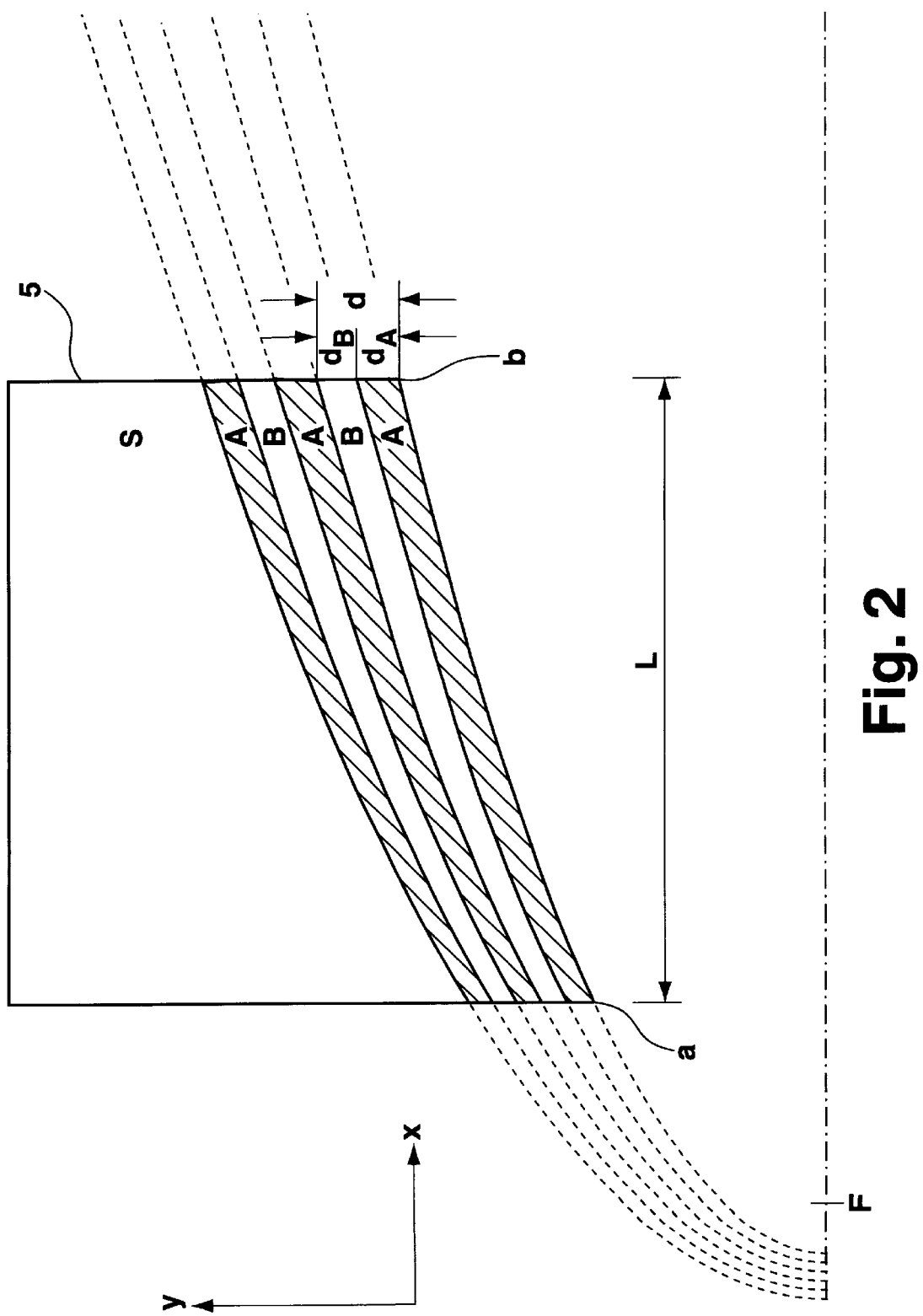
FIG. 2 shows a schematic construction of the curved multilayer Bragg reflector effecting parallelization and monochromatization.

In order to reflect the divergent primary beam 7 which is incident on the parabolically curved multilayer mirror 5 and to convert same into a monochromatic parallel beam 7', the "lattice constant" of the system, given by the period thickness $d=d_A+d_B$ must not be constant. Rather, the period thickness d must change along the length of the reflector 5 in such a fashion that X-ray radiation of a certain wavelength always fulfills the Bragg equation independent of th e point of incidence and angle of incidence. FIG. 2 shows the increase in the period thickness d with length L of the reflector 5 in the x direction, in a highly exaggerated manner. In practical applications, the period thickness d for a W/Si reflector and for Cu-K$\alpha$ radiation a t point a is e.g. d(a)=4 nm.

Figure 3:
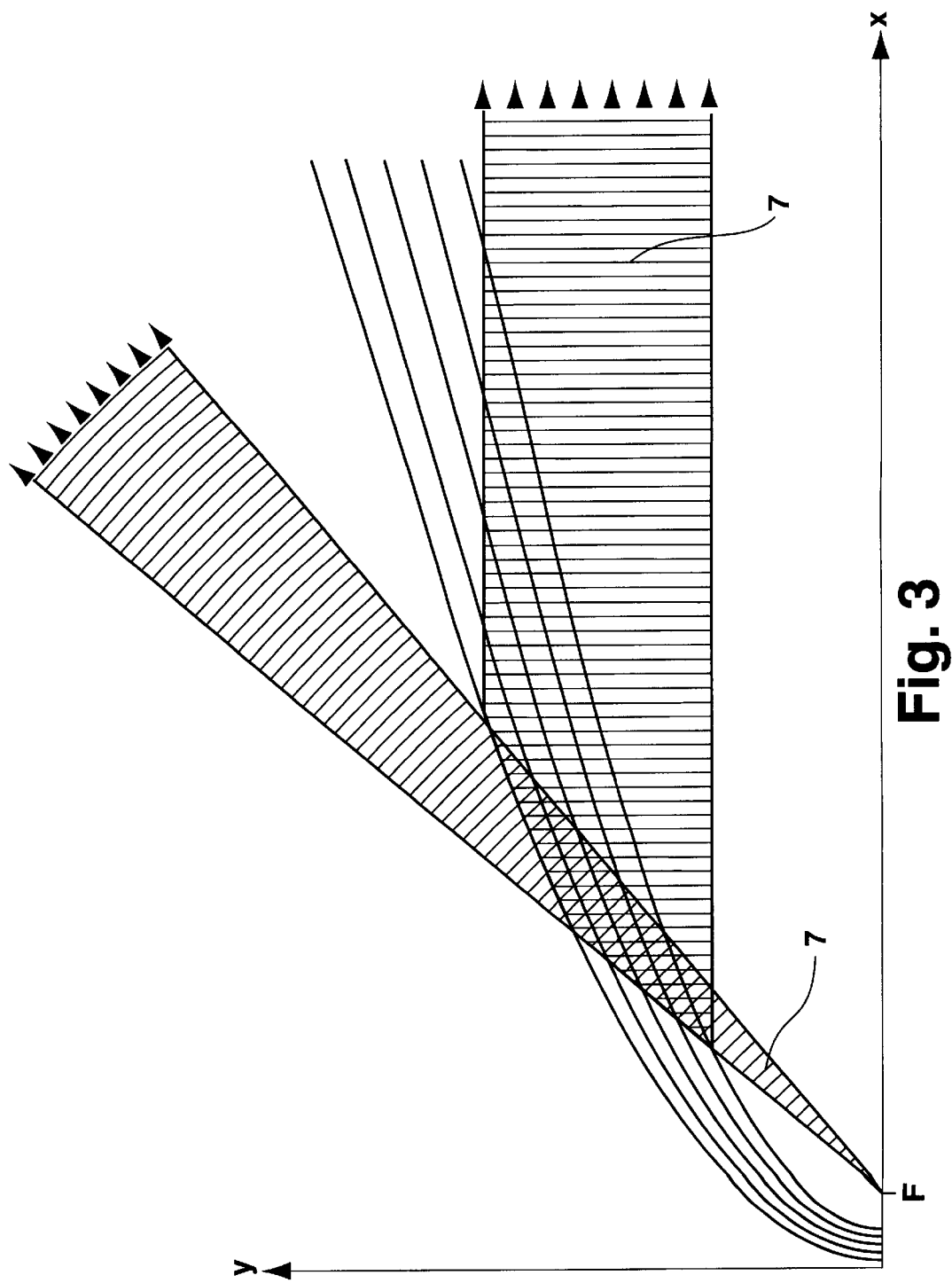
FIG. 3 shows a schematic optical path on a multilayer Bragg reflector in accordance with FIG. 2.

This thickness the n increases in accordance with equations (5) and (6) with the length L and assumes the value, at point b of d(b)=5 nm (see also FIG. 3). The X-ray optical properties of such a multilayer system designated as "graded Bragg structure" are more closely described in SPIE Vol. 563, Applications of Thin-Film Multilayered Structures to Figured X-Ray Optics (1985), pages 114–134.

The layer-sided surface of the substrate S has, as schematically shown in FIG. 2, a curvature in the xy plane in accordance with the equation $y^2=2$ px with p≈0.1 mm. A paraboloid-shaped concave cavity for the substrate S is thereby obtained whose shape is followed by the introduced layers A, B.

The dot-dashed line is the symmetry axis of the parabola, having the focus F, parallel to the x direction. For a point source, the reflector 5 preferentially has the shape of a rotational paraboloid about the dot-dashed symmetry axis of the parabola shown. For a line source, the reflector 5 preferentially has the shape of a parabolic cylinder. In principle, all paraboloids of intermediate shapes are conceivable.

A multilayer Bragg reflector 5 at approximately 150 mm separation from the focal point of the tube 6 and approximately 60 mm in length can, e.g. detect Cu Kα radiation having a beam divergence of approximately 0.5° and reflect same with approximately 80% of the original beam intensity in an approximately 1 mm wide parallel and monochromatic beam.

FIG. 3 schematically shows the optical path at the paraboloid X-ray mirror 5 according to FIG. 2. The X-radiation emanating from the line-shaped source positioned perpendicular to the plane of the drawing at focus F is diffracted in such a fashion by the parabolic Bragg lattice of the graded multilayer mirror 5 that a reflected parallel beam 7' is produced.

Figure 4A:
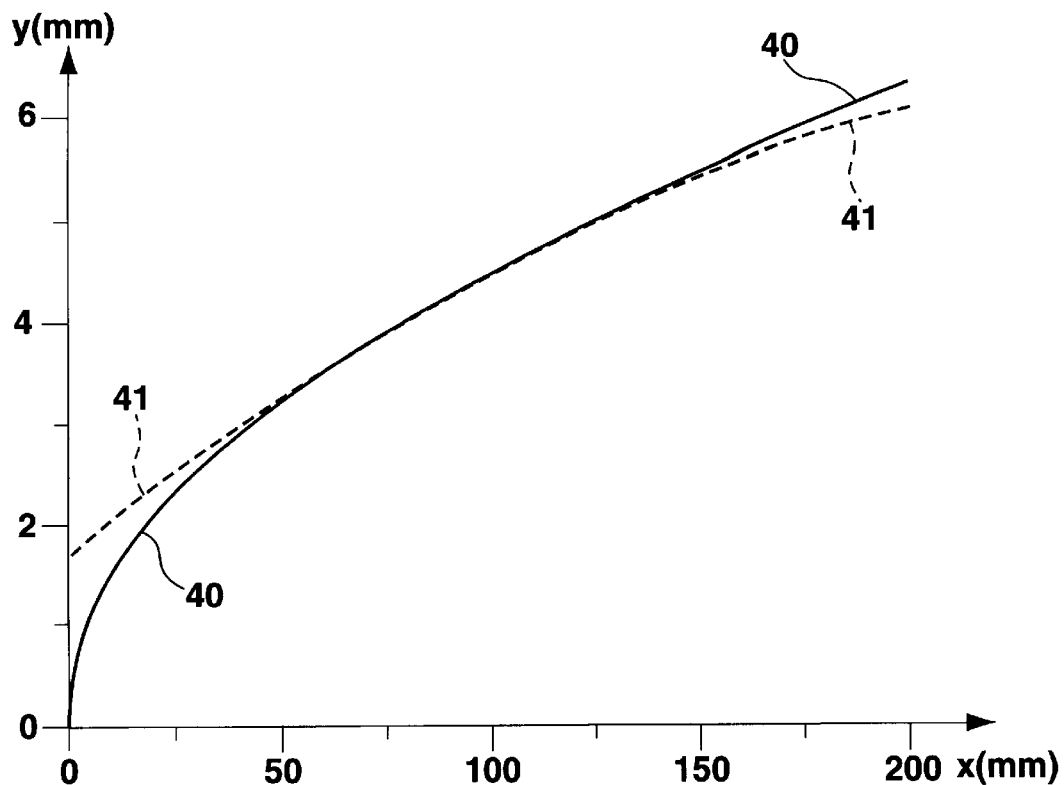
FIG. 4a shows an example of the so-called spherical aberration when approximating a parabolic cylindrical mirror having p=0.1 mm with a circular cylindrical mirror having a radius of 7643 mm and a middle point position of ($x_0$=90 mm, $y_0$=−7639 mm)

The precision of the local d value as well as the precision of the parabolic shape of the curved multilayer Bragg reflector 5 is particularly important for the performance of the X-ray analysis apparatus in accordance with the invention. In order to visualize possible optical error, the so-called spherical aberration is shown in FIG. 4a as a circular shape 41 deviation from the parabolic shape 40 (strongly exaggerated). The curves 40 and 41 intersect at a value of x=90 mm. In the example shown, the parabola 40 follows the formula $y^2=2px$, with p=0.1 mm, whereas the circle (the sphere) 41 has a radius of 7.643 m.

This so-called spherical aberration bears emphasis in connection with the required shape precision of the paraboloid reflector 5, since in practically all optics applications having near axis beams, the errors created by the spherical deviation from paraboloid shape are usually accepted. However, in the present X-ray analysis apparatus in accordance with the invention, the X-ray radiation 7 is incident on the curved surface of the reflector 5 at a grazing incident angle θ≈1°, which leads to substantial imaging errors in the presence of spherical aberration.

Figure 4B:
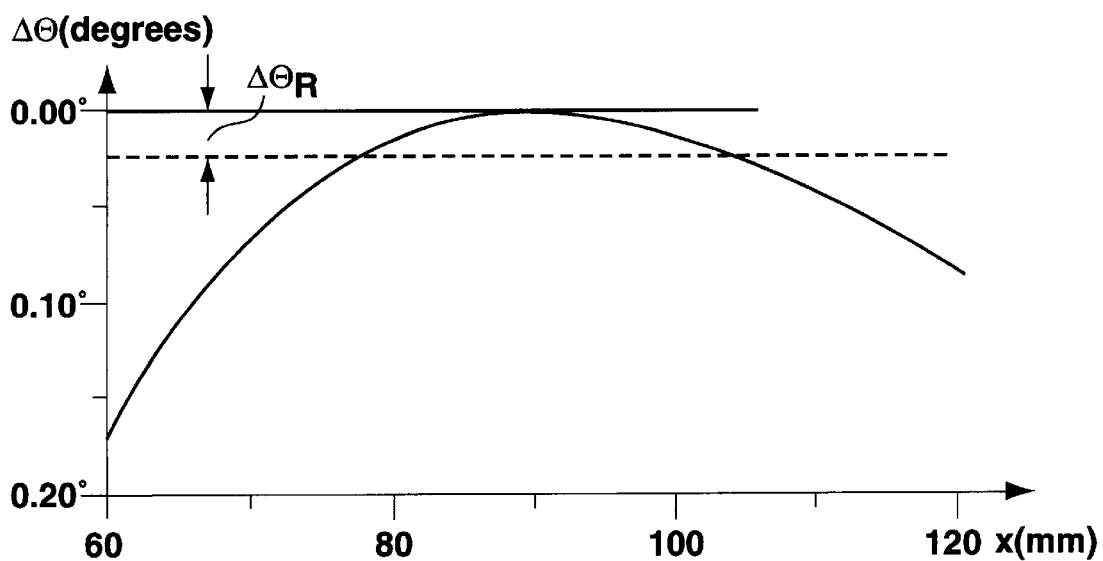
FIG. 4b shows the beam deflection $\Delta\theta$ due to the spherical aberration for the circular cylindrical mirror shown in FIG. 4a in the region of 60 mm≦x≦120 mm.

FIG. 4b schematically shows the beam deflection Δθ as a function of a separation x of the point of incidence due to the spherical aberration, assuming a reflector having the spherical curve 41 shown in FIG. 4a. The acceptable limiting value of the beam deflection $\Delta\theta=\frac{1}{2}\Delta\theta_R$ is shown as a dashed line. A nearly complete intensity loss for the reflected beam already occurs at this limiting value.

Accordingly, the following requirements for a curved multilayer Bragg reflector 5 for use in an X-ray analysis apparatus in accordance with the invention are specified:

1. The desired precision of the deposition (How precise must the d-value and focal distance x be when one assumes that the substrate has a perfect shape?)

The maximal d-value deviation at a given focal distance is given by $$\Delta d/\Delta x=0.5 d/x$$

For Cu Kα X-radiation (λ=0.154 nm, E=8045 eV), typically used for diffractometry, and with a mirror comprising alternating layers of W and Si for a parabolic parameter p=0.1 mm with an average focal distance $x_0$ from the X-ray source, the following maximum allowable deviations from the ideal d(x) relationship defined in equations (5) and (6) above result:

$$\Delta d/\Delta x=0.018 \text{ nm/mm}$$

for $x_0$=90 mm $$\Delta d/\Delta x=0.014 \text{ nm/mm}$$

for $x_0$=150 mm

The ideal d(x) relationship is given by equations (5) and (6) above.

In the region of interest between f=70 . . . 110 mm or 120 . . . 180 mm, d(x) is nearly linear.

2. Shape precision of the parabola (What angular error can the parabola have in order that the outgoing beam has a divergence increase which is small compared to the inherent divergence?)

The full width half maximum $\Delta\theta_R$ of the Bragg reflection from a multilayer assumes values of $\Delta\theta_R=0.232\ \lambda d(\Phi_A-\Phi_B)$ [see AIP Conf. Proc. (USA) 75(1981 170–178].

For Cu Kα X radiation (λ=0.154 nm, E=8045 eV), typically utilized in diffractometry, a mirror consisting of W/Si multilayer (A=W, B=Si) and having a parabolic parameter p=0.1 mm gives, for a focal distance x from the X-ray source, the following maximum allowable angular errors of 0.5 $\Delta\theta_R$ for the parabolic multilayer:

| [mm] | d [nm] | 0.5Δθ_R |
|---|---|---|
| 60 | 2.667 | 0.023° |
| 80 | 3.080 | 0.027° |
| 100 | 3.444 | 0.030° |
| 120 | 3.772 | 0.033° |

We note that the values 0.5 $\Delta\theta_R$ given in the table lead to nearly complete intensity loss. Ground parabolic mirrors can be produced with an angular error of ≦1 arcsec=0.00028°.

The above mentioned angular tolerance require a precise parabolic shape. The degree of error which would occur if one uses a circular shape rather than a parabola can be seen from FIG. 4b.

3. Roughness and substrate surface (From which differing heights can the beam be reflected so that destructive interference in the emerging beam does not cause a significant intensity loss?)

$\Delta y=\lambda/4(4\pi \sin\theta)=d/2\pi$ (the limiting value for a 1/e decay, e.g. 63% intensity loss).

For a Cu Kα (λ=0.154 nm, E=8045 eV), usually utilized in X ray diffractometry, and a mirror comprising alternating layers of W and Si (A=W, B=Si) with a parabolic parameter p=0.1 mm, the following maximum allowable deviation Δy from the ideal parabolic shape results at a focal distance x from the X ray source:

| x [mm] | d [nm] | Δy [nm] |
|---|---|---|
| 60 | 2.667 | 0.42 |
| 80 | 3.080 | 0.49 |
| 100 | 3.444 | 0.55 |
| 120 | 3.772 | 0.60 |

Dynamic calculations using Fresnel theory give more accurate values which are, however, of similar magnitude. Ground parabolic mirrors can be produced from quartz with an RMS roughness of ≦0.5 nm. RMS roughness values of 0.3 nm can be regularly achieved.

Figure 5:
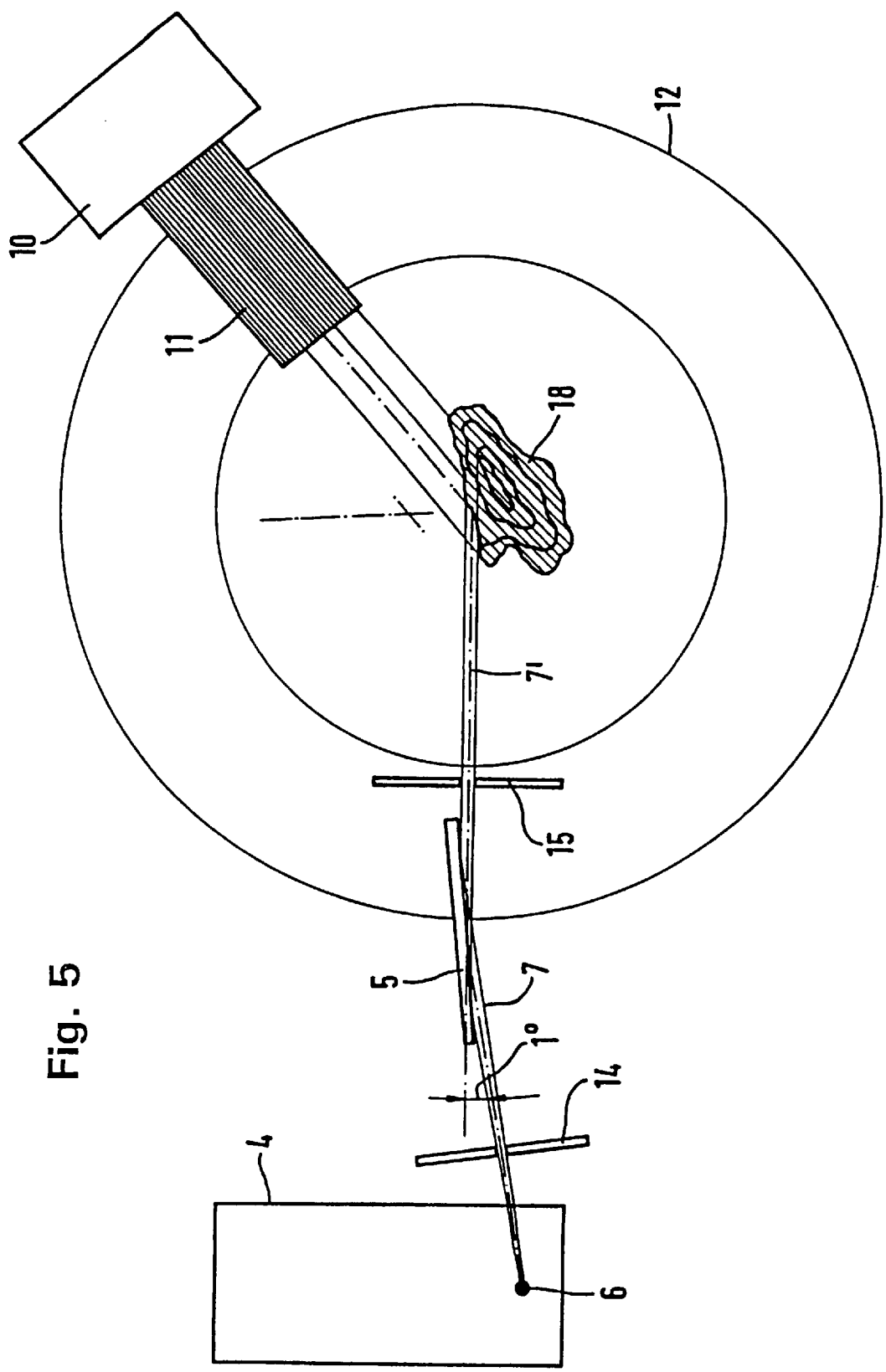
FIG. 5 is an additional embodiment of the X-ray analysis apparatus in accordance with the invention for the measurement of massive work pieces of irregular shape.

Due to the parallel beam X-ray optics realized in the analysis apparatus in accordance with the invention, the sample geometry has no influence on the angular precision and angular resolution of the associated measurement. Even massive work pieces 18 of arbitrary shape (shaped components), broken surfaces, corroded surfaces, or excavated objects, which must remain unchanged, can thereby be investigated using the diffractometer shown in FIG. 5. Technical products such as rigid parts or surface coatings of machine parts much often be analyzed in their given shape when their material properties are to be preserved. Many materials, including art objects and archeological specimens, have irregularly shaped surfaces which must be investigated non-destructively.

Figure 6:
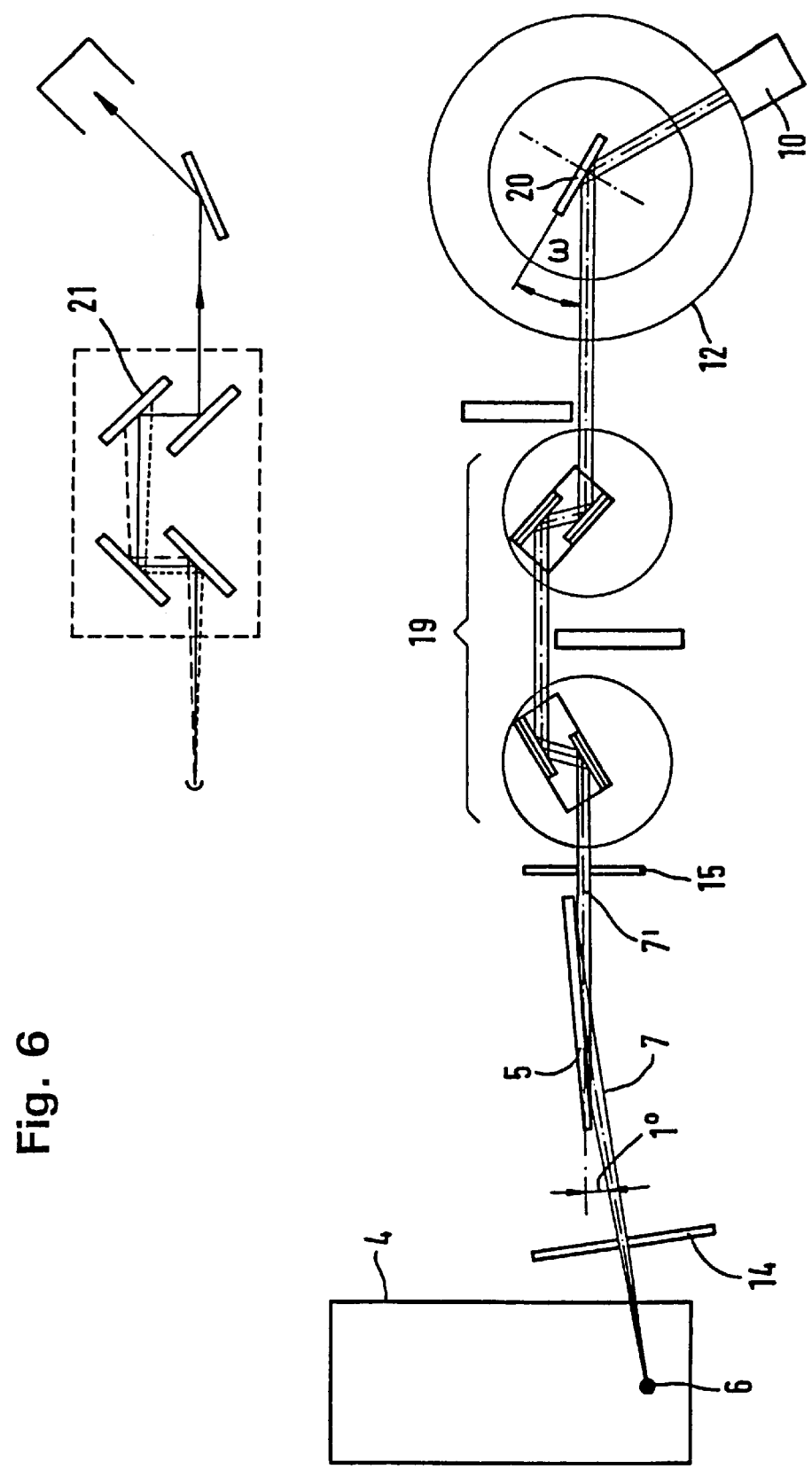
FIG. 6 is an embodiment of a multiple "channel cut" monochromator of type (+−−+)

In the parallel beam multi-crystal diffractometer shown in the bottom portion of FIG. 6, the multilayer Bragg reflector 5, serving as a condenser, has, e.g. a downstream "channel cut" monochromator 19, per se known in the art from U.S. Pat. No. 4,567,605 which deflects the parallel primary beam 7' in the direction of the sample 20 disposed in the center of a high-resolution omega goniometer. Since a parallel beam is incident into the monochromator 19, nearly the entire primary beam intensity is transmitted. In contrast thereto, the conventional multi-crystal diffractometers having divergent beam optical paths (see FIG. 6 above) lose more than 90% of the primary beam intensity during reflection at the third monochromator crystal 21.

Figure 7:
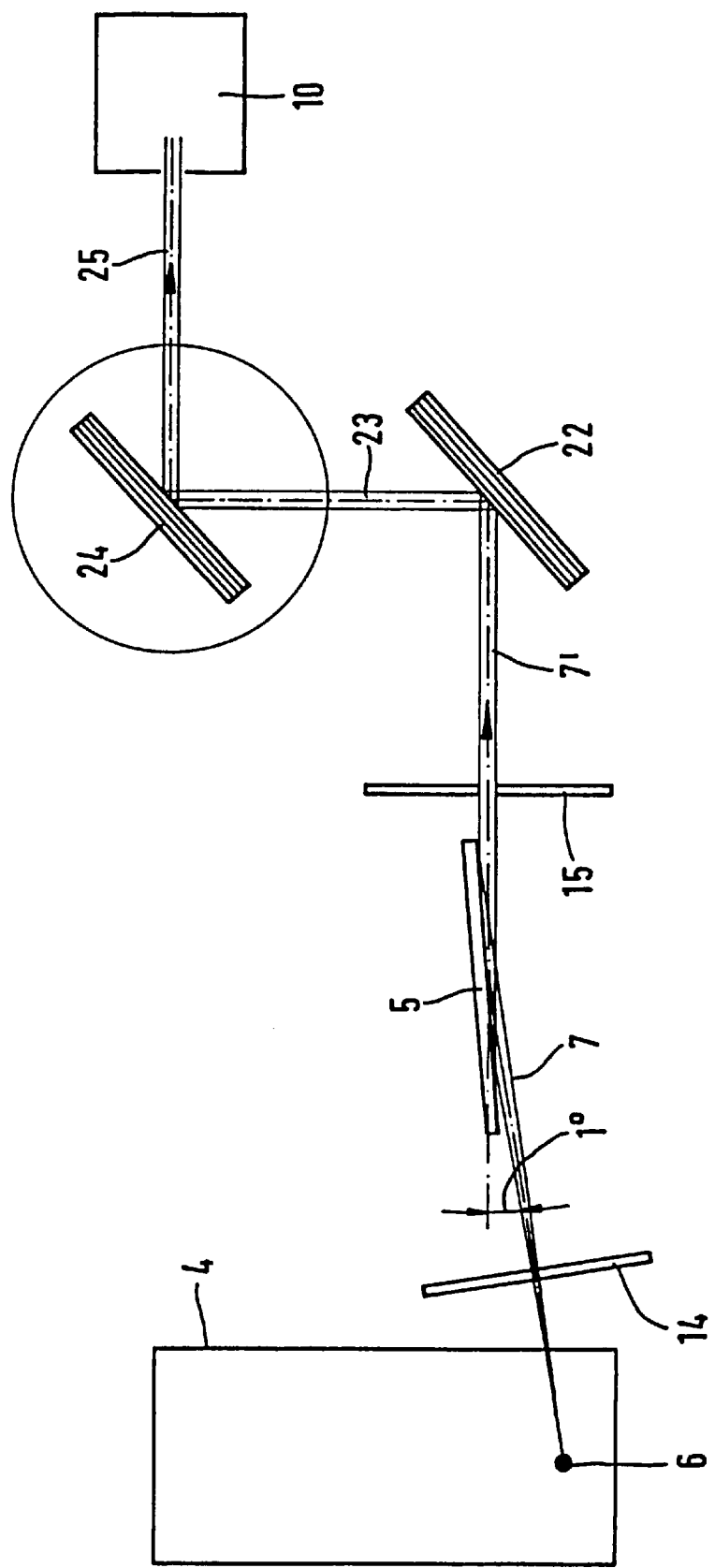
FIG. 7 is an embodiment having a second Bragg reflector.

Two-crystal-diffractometers are suitable for highly precise investigations of the actual structure of single crystals in comparison to an ideal reference crystal. In order to also be able to realize a parallel beam X-ray optics in such an apparatus, a multilayer Bragg reflector 5, functioning as a condenser, is disposed in the optical path between the X-ray tube 4 and a reference crystal 22 of high purity, as is schematically shown in FIG. 7. The radiation 23 Bragg-reflected from the reference crystal 22 is then incident as a parallel beam, on the sample 24 where it is then once more diffracted and, finally, detected as a parallel beam 25 in the detector 10.

Figure 8:
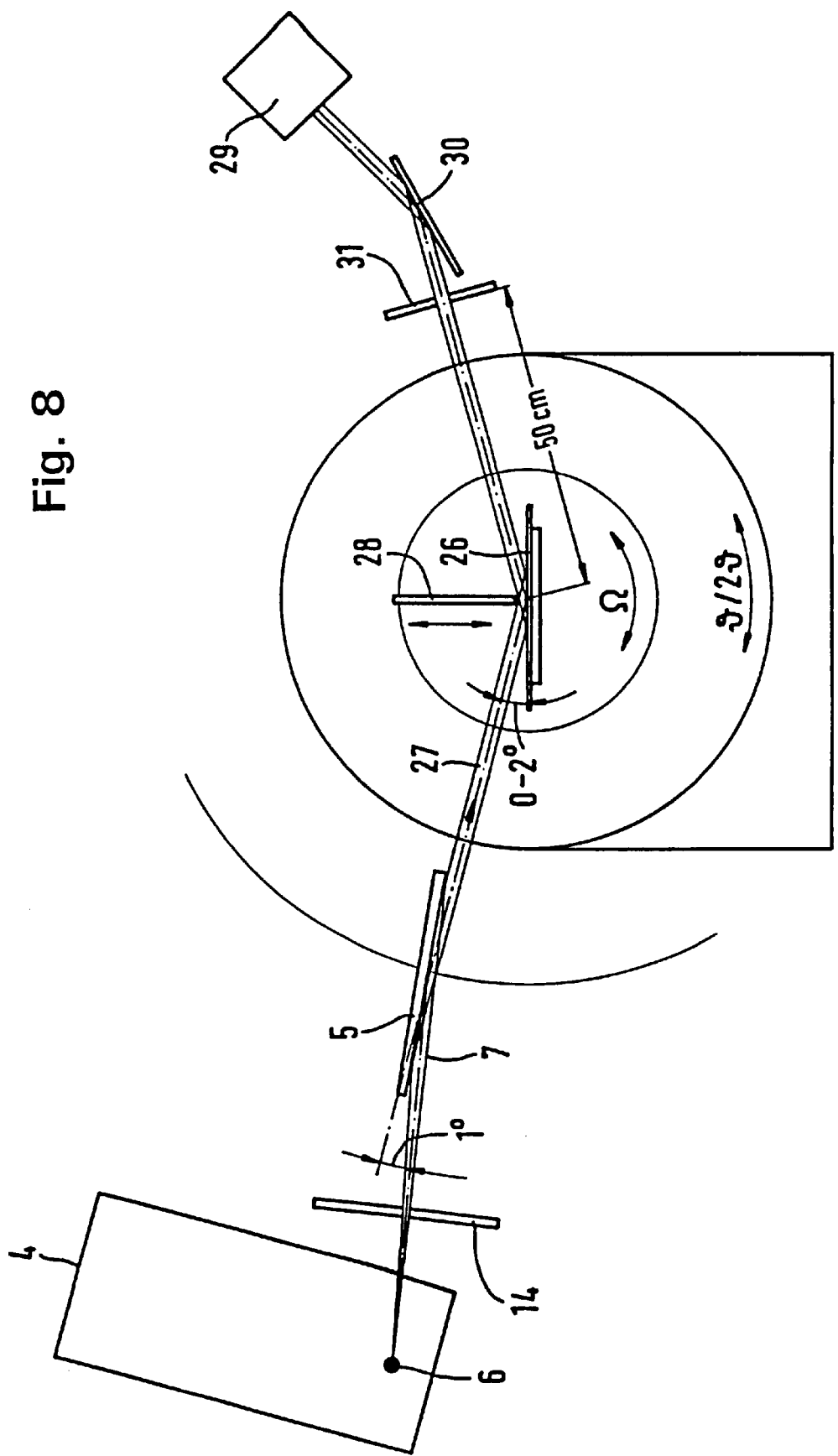
FIG. 8 is an embodiment with a second monochromator.

In particular, thin layers 26 and smooth surfaces can be investigated with the parallel beam reflectometer shown in FIG. 8, wherein one can vary the size of the region illuminated by the parallel primary beam 27 with the assistance of a collimator 28 which can be displaced in the direction of the arrow. A flat monochromator 30 disposed upstream of a scintillation counter 29 serves for suppression of undesirable scattered radiation. It is disposed directly behind a collimator 31 whose separation from the sample 26 is approximately 50 cm.

Figure 9:
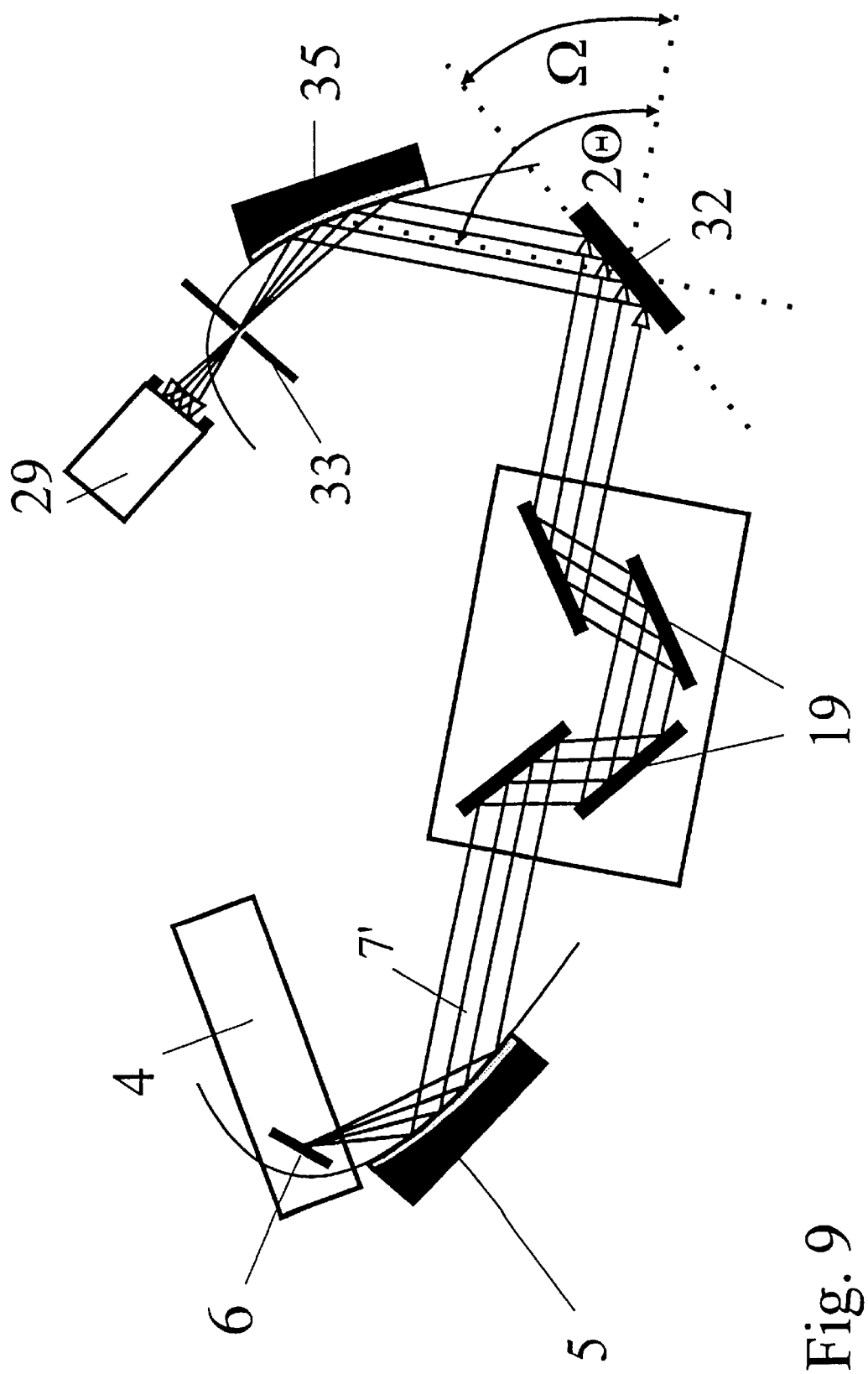
FIG. 9 is an embodiment with a second curved multilayer Bragg reflector and a "channel cut" monochromator.

FIG. 9 shows an embodiment of the X-ray analysis apparatus in accordance with the invention with which a "channel cut" monochromator 19 is disposed downstream, as seen in the direction of the reflected parallel radiation beam 7', of the first multilayer Bragg reflector 5 which is, in principle, of the same construction as shown in FIG. 6. A sample 32 is downstream thereof. The radiation reflected from the sample 32 at an angle 2θ is incident at a flat angle onto a second curved multilayer Bragg reflector 35, having the same construction as the first reflector 5, whose paraboloid opening is directed towards the sample 32. A collimator 33 is positioned at the focal point of the second reflector 35 between same and the detector 29.

The configuration in accordance with FIG. 9 facilitates detection of the radiation diffusely reflected from the sample 32 in selective accordance with its wavelength and exit direction, since the combination of the second multilayer Bragg reflector 35 and the collimator 33 disposed at the focal point thereof serves as an analyzer.

Figure 10:
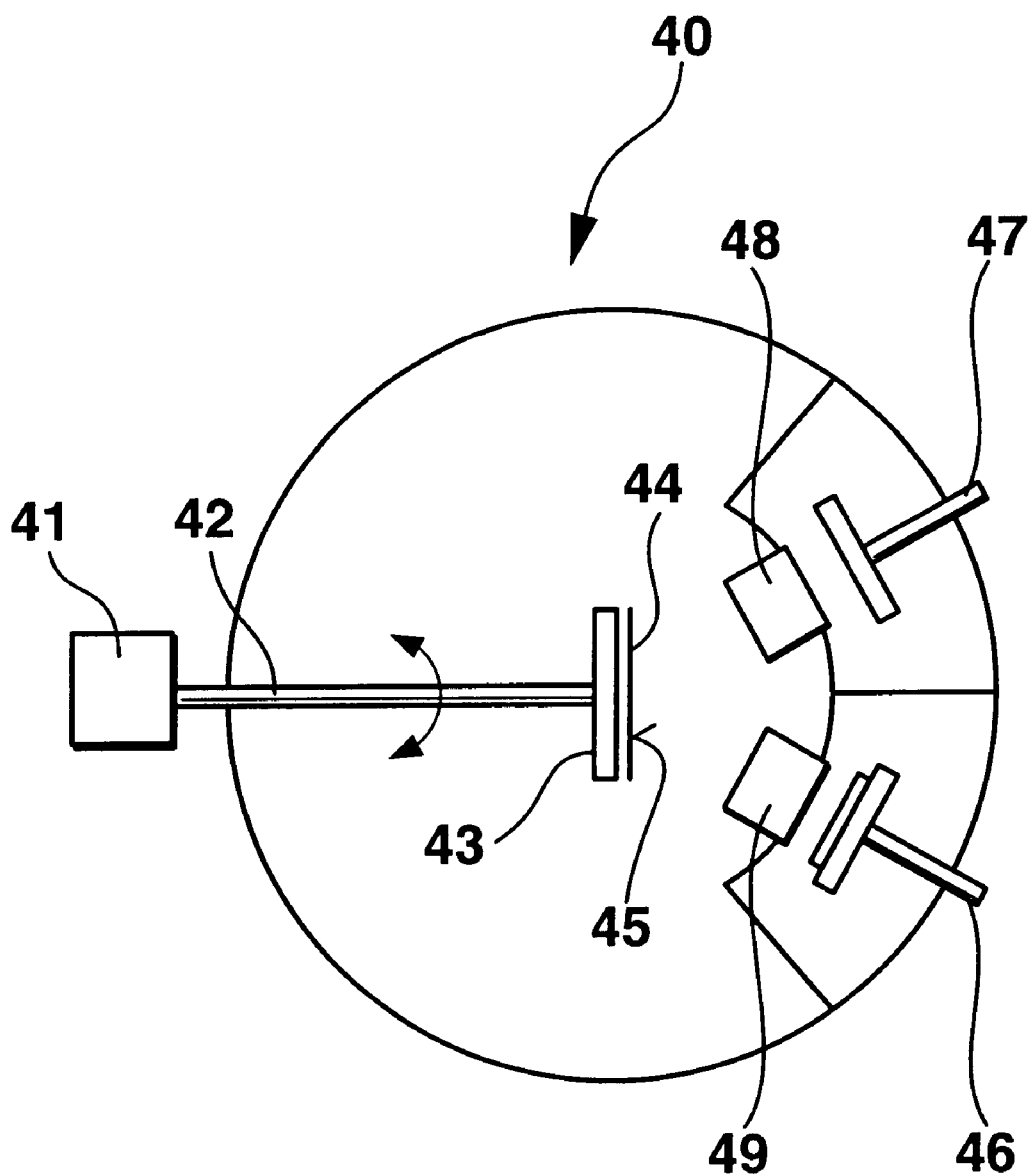
FIG. 10 sketches an apparatus for producing the mirror in accordance with the invention.

FIG. 10 shows an apparatus 40 suitable for producing the mirror in accordance with the invention. The apparatus 40 comprises means for rotating 41 an elongated rod 42 about an axis thereof. The rod 42 is joined to a substrate holder 43 which rotates in response to the rotating means 41 as transmitted by the elongated rod 42. A substrate 44 having a curved surface 45 is mounted to the substrate holder 43 and rotates along therewith. In a first rotation position of the apparatus, a heavy material is sputtered from sputter source 46, collimated and/or focussed by collimating means 49, and directed onto the surface 45 of the substrate. After a heavy layer has been deposited on the surface of the substrate 45, the rotating means 41 rotate the substrate 44 through approximately 180°. The collimating means 49 are activated to shut-off the beam emanating from sputtering source 46. Sputtering source 47 is then activated, by means of collimating and blocking means 48, to deposit a light material onto the surface of the substrate 45. The non-orthogonal positionings of the sputtering sources 46 and 48 provide a changing solid angle for the substrate 44 relative to the sources 46 and 48 respectively which automatically results in a changing layer thickness along an x direction perpendicular to the rod 42 and lying substantially in the plane of the sources 46 and 48.

In detail, the sputtering apparatus 40 comprises a vaccuum system equipped with two sputtering sources 46 and 48 as well as the sample holder 43 which is configured for various applications and which allows rotation as well as heating and cooling of the substrate by means of an appropriate substrate holder 43. The off-normal geometry between the sources 46 and 48 and the substrate 44 effects a varying distance between the sources 46 and 48 and the substrate 44 across the substrate surface 45 leading to a layer thickness gradient. This effect can be used to fabricate multilayers of laterally graded periods. In a preferred embodiment, the sputtering gas is argon at a pressure in the range 0.1 to 0.5 Pa. The sputtering system 40 is characterized by extremely high precision and reproducibility of the sputtering rate and can produce multilayer depositions having multilayer periods with 1% precision. This precision can be maintained and reproduced in subsequent depositions. The interface quality can be optimized by taking into account the thermodynamics and kinetics of thin film reactions as previously investigated (see e.g. C. Michaelsen, K. Barmak, and T. P. Weihs, J. Phys. D. Applied Physics, 30 (1997) 3167.

We claim:

1. An X-ray analysis apparatus for analysis of a sample, the apparatus comprising:

a source emitting X-radiation;

a detector sensitive to X-radiation;

at least one of beam-shaping and beam-limiting means; and a curved multilayer Bragg reflector disposed in an optical path between said source and the sample, and including a periodically repeating sequence of layers, wherein a period comprises at least two individual layers A, B having different index of refraction decrements $\delta_A \neq \delta_B$ and having thicknesses $d_A$ and $d_B$, wherein a period thickness, a sum $d=d_A+d_B+d_C+ \ldots$ of individual layers A, B, C, . . . of a period, changes constantly along an x direction and wherein said reflector is curved in such a fashion that it forms a partial surface of a paraboloid at one of a focal line and focal point of which, said source or an image of said source is disposed so that a parallel beam is produced subsequent to reflection and wherein said layers of said reflector are directly disposed on a concave curved surface of a paraboloid-shaped hollow substrate (S) through one of evaporation, sputtering and growth, wherein a curvature of said concave substrate surface, in an xy cross section, is given by $$y^2 = 2px$$

with one of 0.02 mm<p<0.5 mm, and p≈0.1 mm, and
wherein a concave substrate surface facing said reflector has a maximum allowable shape deviation of $$\Delta p = \sqrt{2px} \cdot \Delta\theta_R,$$

wherein $\Delta\theta_R$ is a full width half maximum of Bragg reflection of said reflector and assumes values of $$0.01° < \Delta\theta_R < 0.5°,$$

and one of $$0.02° < \Delta\theta_R < 0.20°,$$

and wherein said concave substrate surface facing said reflector has a maximum allowable irregularity of $$\frac{\Delta y}{\Delta x} = \frac{1}{2}\Delta\theta_R,$$

and wherein said concave substrate surface facing said reflector has a maximum allowable roughness of one of $$\Delta y = \frac{d}{2\pi}, \text{ and } \Delta y \leq 0.3 \text{ nm,}$$

and said X-ray radiation is incident on a curved surface of said reflector at an angle of incidence $$0° < \theta \leq 5°,$$

and said period thickness d changes along an x direction in such a fashion that said X-ray radiation of a particular wavelength λ from a point or line X-ray source always experiences Bragg reflection independent of a point of incidence (x, y) on said reflector, wherein said period thickness d increases towards a paraboloid opening in said x direction in accordance with $$d = \frac{\lambda}{2} \frac{1}{(1-\bar{\delta}/\sin^2\theta)\sin\theta}$$

with $\theta = \text{arccot}\sqrt{\frac{2x}{p}}$ wherein $\bar{\delta}$ is a decrement of an average index of refraction of said multilayer Bragg reflector and
a deviation per length $\Delta d/\Delta x$ of said period thickness d at each point of said multilayer Bragg reflector along said x direction is smaller than $$\frac{\Delta d}{\Delta x} = \frac{1}{2}\frac{d}{x}, \text{ and}$$

1 nm ≤ d ≤ 20 nm, and
a number N of periods is one of 10<N<500, and 50 ≤ N ≤ 100, and
an energy E of quanta of said X-radiation is 0.1 keV<E<0.1 MeV.

2. The X-ray analysis apparatus of claim 1, further comprising means for at least one of high-resolution spectrometry and diffractometry.

3. The X-ray analysis apparatus of claim 1, wherein said beam shaping means comprise a collimator disposed in an optical path between said source, the sample and said detector, said collimator having fins extending parallel to each other and pointing towards a radiation direction of said X-radiation.

4. The X-ray analysis apparatus of claim 1, further comprising a first monochromator disposed in an optical path between said curved reflector and the sample.

5. The X-ray analysis apparatus of claim 4, wherein said first monochromator is one of a multiple monochromator, and a channel cut monochromator.

6. The X-ray analysis apparatus of claim 1, further comprising a second multilayer Bragg reflector disposed in an optical path between said curved reflector and the sample.

7. The X-ray analysis apparatus of claim 4, further comprising a second monochromator disposed in an optical path between the sample and said detector.

8. The X-ray analysis apparatus of claim 7, wherein said second monochromator is a flat crystal monochromator.

9. The X-ray analysis apparatus of claim 1, further comprising an additional curved multilayer Bragg reflector disposed in an optical path between the sample and said detector, said additional Bragg reflector having a same construction as said curved multilayer Bragg reflector, and having a paraboloid opening directed towards the sample, wherein said beam shaping means comprises a collimator positioned at a focal point of said additional reflector between said additional reflector and said detector.

10. A curved multilayer Bragg reflector for an X-ray analysis apparatus having a source emitting X-ray radiation, a sample to be analyzed, a detector sensitive to X-ray radiation, and at least one of beam-shaping and beam-limiting means, the Bragg reflector disposed in an optical path between the source and the sample, the Bragg reflector comprising:
a periodically repeating sequence of layers, wherein a period comprises at least two individual layers A, B having different index of refraction decrements $\delta_A \neq \delta_B$ and having thicknesses $d_A$ and $d_B$,
wherein a period thickness, a sum $d = d_A + d_B + d_C + \ldots$ of individual layers A, B, C, ... of a period, changes constantly along an x direction and
wherein said reflector is curved in such a fashion that it forms a partial surface of a paraboloid at one of a focal line and a focal point of which, said source or an image of said source is disposed so that a parallel beam is produced subsequent to reflection and,
wherein said layers of said reflector are directly disposed on a concave curved surface of a paraboloid-shaped hollow substrate through one of evaporation, sputtering and growth, wherein a curvature of said concave substrate surface, in an xy plane, is given by $$y^2 = 2px$$

with one of 0.02 mm<p<0.5 mm, and p≈0.1 mm, and wherein a concave substrate surface facing said reflector has a maximum allowable shape deviation of $$\Delta p = \sqrt{2px} \cdot \Delta\theta_R,$$

wherein $\Delta\theta_R$ is a full width half maximum of Bragg reflection of said reflector and assumes values of one of $$0.01° < \Delta\theta_R < 0.5°,$$

and $$0.02° < \Delta\theta_R < 0.20°,$$

and said concave substrate surface facing said reflector having a maximum allowable waviness of $$\frac{\Delta y}{\Delta x} = \frac{1}{2}\Delta\theta_R,$$

and said concave substrate surface facing said reflector having a maximum allowable roughness of one of $$\Delta y = \frac{d}{2\pi}, \quad \text{and} \quad \Delta y \leq 0.3 \text{ nm},$$

and said X-ray radiation being incident on a curved surface of said reflector at a n angle of incidence $0° < \theta \leq 5°$, wherein said period thickness d changes along an x direction in such a fashion that said X-radiation of a particular wavelength λ from a point or line X-ray source always experiences Bragg reflection independent of a point of incidence (x, y) on said reflector, wherein said period thickness d increases towards a paraboloid opening in said x direction in accordance with $$d = \frac{\lambda}{2}\frac{1}{(1-\bar{\delta}/\sin^2\theta)\sin\theta}$$

with $\quad \theta = \text{arccot}\sqrt{\frac{2x}{p}}$ wherein $\bar{\delta}$ is a decrement of an average index of refraction of said multilayer Bragg reflector and
a deviation Δd/Δx of said period thickness d at each point of said multilayer Bragg reflector along said x direction is smaller than $$\frac{\Delta d}{\Delta x} = \frac{1}{2}\frac{d}{x}, \quad \text{and}$$

$$1 \text{ nm} \leq d \leq 20 \text{ nm},$$

and wherein one of the following conditions obtain for the number N of periods:
$10 < N < 500$, and $50 \leq N \leq 100$ with N being a a number of periods and wherein
$0.1$ keV $< E < 0.1$ MeV with E being an energy of quanta of the X-radiation.

11. The Bragg reflector of claim 10, wherein said substrate is made from one of amorphous and polycrystalline material.

12. The Bragg reflector of claim 11, wherein said substrate is made from one of glass, amorphous silicon, ceramic material, plastic, and fused quartz.

13. The Bragg reflector of claim 10, wherein said substrate has a thickness D sufficient to effect a mechanical support body for the reflector and having a stable shape, wherein $0.05$ L $< D < 0.5$ L with L being a length of the substrate in an x direction.

14. The Bragg reflector of claim 10, wherein a number n of individual layers A, B, C, . . . per period is $2 \leq n \leq 4$.

15. The Bragg reflector of claim 14, wherein n=2 and wherein a layer thickness of a first layer $d_A$ and a thickness of a second layer $d_B$ are related by $d_A \cdot 0.95 \leq d_B \leq d_A \cdot 1.05$.

16. The Bragg reflector of claim 14, wherein n=2 and a first layer comprises a heavy element and a second layer comprises a light element, wherein said heavy element is selected from the group consisting of Cu, Ni, Co, Fe, Au, Pd, Mn, Cr, Mo, V, Ti, Zr, Rh, Ag, Sn, and W and said light element is selected from the group consisting of B, C, Si, N, Mg, O, and Al.

17. The Bragg reflector of claim 14, wherein n=2 and a first layer comprises one of a heavy alloy, a heavy element and a heavy compound and said second layer comprises one of a light alloy, a light element and a light compound, wherein said first layer comprises an element selected from the group consisting of Cu, Ni, Co, Fe, Au, Pd, Mn, Cr, Mo, V, Ti, Zr, Rh, Ag, Sn, and W, wherein said second layer comprises an element selected from the group consisting of B, C, Si, N, Mg, O and Al.

18. A method for producing the Bragg reflector of claim 10, the reflector having a curved multilayer structure comprising at least two individual layers A, B, having differing index of refraction decrements and having thicknesses dA and dB, wherein a period thickness d=dA+dB+dC+ . . . of individual layers A, B, C . . . changes monotonically in an x direction, the method comprising the steps of:
   a) mounting a substrate, having a parabolic substrate surface, for rotation about an axis extending substantially normal to a region of said substrate surface;
   b) depositing said substrate surface with a heavy beam of sputtered material emanating from a first sputter source, said first sputter source disposed at a first side of said axis, said heavy beam having a direction forming a first acute angle with said axis;
   c) rotating said substrate about said axis through approximately 180°; and
   d) depositing said substrate, following steps b) and c), with a light beam of sputtered material emanating from a second sputter source, said second sputter source disposed at a second side of said axis opposite said first side, said light beam having a direction forming a second acute angle with said axis.

19. The method of claim 18, wherein steps b) and d) comprise the steps of at least one of focussing, collimating and blocking said beam of heavy material and said beam of light material.

20. The method of claim 18, further comprising repeating steps b), c), and d) a plurality of times.

21. The method of claim 18, wherein said first angle has a magnitude substantially equal to a magnitude of said second angle.

22. An apparatus for producing the Bragg reflector of claim 10, the reflector having a curved multilayer structure comprising at least two individual layers A, B, having differing index of refraction decrements and having thicknesses dA and dB, wherein a period thickness d=dA+dB+ dC+ . . . of individual layers A, B, C . . . changes monotonically in an x direction, the apparatus comprising:
   a) means for mounting a substrate, having a parabolic substrate surface for rotation about an axis extending substantially normal to a region of said substrate surface;
   b) first means for deposition said substrate surface with a beam of heavy sputtered material emanating from a first sputter source, said first sputter source disposed at a first side of said axis, said beam of heavy material having a direction forming a first acute angle to said axis;

c) means for rotating said substrate about said axis through substantially 180°; and d) second means for deposition of said substrate, following steps c) and d), with a beam of light sputtered material emanating from a second sputter source, said second sputter source disposed at a second side of said axis opposite said first side, said beam of light material having a direction forming a second acute angle to said axis.

23. The apparatus of claim 22, wherein said first and said second deposition means comprise means for at least one of focussing, collimating, and blocking said heavy beam and said light beam.

24. The apparatus of claim 22, wherein said first angle has a magnitude substantially equal to a magnitude of said second angle.

\* \* \* \* \*

UNITED STATES PATENT AND TRADEMARK OFFICE
CERTIFICATE OF CORRECTION

PATENT NO. : 6,226,349 B1
DATED : May 1, 2001
INVENTOR(S) : Manfred Schuster et al.

Page 1 of 1

It is certified that error appears in the above-identified patent and that said Letters Patent is hereby corrected as shown below:

Please replace:

"Assignee: Bruker AXS Analytical X-Ray Systems GmbH, Karlsruhe (DE)" with
-- Assignee: Bruker AXS Analytical X-Ray Systems GmbH,
       Karlsruhe (DE)

GKSS-Forschungszentrum Geesthacht GmbH
       D-21502 Geesthacht (DE) --

Signed and Sealed this

Twenty-eighth Day of August, 2001

Attest:

NICHOLAS P. GODICI
Attesting Officer    Acting Director of the United States Patent and Trademark Office